US007365344B2

(12) United States Patent  
Aoki (10) Patent No.: US 7,365,344 B2  
(45) Date of Patent: Apr. 29, 2008

(54) SCANNING FLUORESCENT MICROSCOPE (75) Inventor: Masahiro Aoki, Tokyo (JP)

(73) Assignee: Olympus Corporation, Tokyo (JP)

( * ) Notice: Subject to any disclaimer, the term of this patent is extended or adjusted under 35 U.S.C. 154(b) by 239 days.

(21) Appl. No.: 11/101,053

(22) Filed: Apr. 6, 2005

(65) Prior Publication Data  
US 2005/0224721 A1    Oct. 13, 2005

(30) Foreign Application Priority Data  
Apr. 9, 2004    (JP)    ............................. 2004-115681

(51) Int. Cl.  
*G01J 1/58* (2006.01)  
*G01N 21/00* (2006.01)

(52) U.S. Cl. ................................ 250/458.1; 250/461.1

(58) Field of Classification Search ............. 250/458.1, 250/461.1, 372  
See application file for complete search history.

(56) References Cited

U.S. PATENT DOCUMENTS

| 4,122,348 | A | * | 10/1978 | Bruck ...................... 250/461.2 |
| 4,827,125 | A | * | 5/1989 | Goldstein .................... 250/234 |
| 5,127,730 | A | | 7/1992 | Brelje et al. |
| 6,025,917 | A | * | 2/2000 | Toyonaga et al. ........... 356/364 |
| 6,376,843 | B1 | * | 4/2002 | Palo ........................ 250/458.1 |
| 2002/0063863 | A1 | * | 5/2002 | Kask ........................... 356/317 |
| 2004/0036870 | A1 | * | 2/2004 | Goix ........................... 356/318 |
| 2004/0119983 | A1 | * | 6/2004 | Brasen et al. ................ 356/492 |
| 2005/0072936 | A1 | * | 4/2005 | Kotani ...................... 250/458.1 |

FOREIGN PATENT DOCUMENTS

JP            8-254654 A      10/1996

OTHER PUBLICATIONS

C.J. DeGrauw et al; "Multiple Time-Gate Module for Fluorescence Lifetime Imaging" ; Applied Spectroscopy; vol. 55, No. 6, pp. 670-678; 2001.  
"Array Fluorometry: The Theory of the Statistical Multiplexing of Single Photon Timing" Time-Resolved Laser Spectroscopy in Biochemistry II; 1990; pp. 26-34.  
"Fluorescence of GFP Found Highly Polarized" Biophotonics International; 2002; p. 10.

* cited by examiner

*Primary Examiner*—David Porta  
*Assistant Examiner*—Casey Bryant  
(74) *Attorney, Agent, or Firm*—Frishauf, Holtz, Goodman & Chick, P.C.

(57)    ABSTRACT

A scanning fluorescent microscope includes a light source which irradiates a sample with an exciting light pulse, and a splitter which splits fluorescent photons emitted from the sample excited by the exciting light pulse, in at least first and second groups. The scanning fluorescent microscope also includes first and second detectors which detect the fluorescent photons of the first and second group, respectively, first and second counters which count numbers of fluorescent photons detected by the detectors, respectively, first and second correcting units which perform a predetermined correction to the numbers of fluorescent photons, an adder adding the numbers of fluorescent photons corrected, and an operating unit which calculates a florescent lifetime based on resulting numbers from the adder.

18 Claims, 7 Drawing Sheets

SCANNING FLUORESCENT MICROSCOPE

CROSS-REFERENCE TO RELATED APPLICATIONS

This application is based upon and claims the benefit of priority from Japanese Patent Application No. 2004-115681, filed Apr. 9, 2004, the entire contents of which are incorporated herein by reference.

This application is related to the following commonly assigned applications: U.S. Ser. No. 10/769,135 filed Jan. 30, 2004; U.S. Ser. No. 10/741,522 filed Dec. 18, 2003, all of which are incorporated herein by reference.

BACKGROUND OF THE INVENTION

1. Field of the Invention

The present invention relates to a scanning fluorescent microscope that irradiates a sample with exciting light pulses, counts the number of fluorescent photons emitted from the excited sample, and measures at least a fluorescent lifetime based on the counted number of the fluorescent photons.

2. Description of the Related Art

To examine the excited state of a sample, a conventionally known technique includes irradiating the sample with exciting light to turn the sample into an excited state, measuring the fluorescence emitted from the sample during the transition from the excited state to the ground state, and calculating the fluorescent lifetime. One known method of calculating a fluorescent lifetime is a Time-Gate Technique, according to which a sample is irradiated with exciting light pulses, the number of fluorescent photons emitted from the sample is measured at plural periods of time, and the fluorescent lifetime is calculated based on the measured numbers of fluorescent photons (see C. J. DE GRAUW and H. C. GERRITSEN, "Multiple Time-Gate Module for Fluorescence Lifetime Imaging", APPLIED SPECTROSCOPY, Volume 55, Number 6, 2001).

In order to minimize the error in fluorescent lifetime calculation, measurement should be conducted on a large number of fluorescent photons. However, an increase in the emission rate of fluorescent photons with an increase in the intensity of the exciting light results in an increase in the measurement error of the lifetime. This is because that the fluorescent photons successively entering a measurement device cannot be captured within the measurement resolution thereof. Hence, for the minimization of the error in fluorescent lifetime calculation, the number of emitted fluorescent photons per one irradiation of exciting light (emission rate) needs to be equal to or less than 0.01. In other words, calculation of fluorescent lifetime is extremely time-consuming when error minimization is required. In addition, in calculation of the fluorescent lifetime of a living body, for example, in which the fluorescent lifetime changes over time, the speed of calculation cannot outpace the speed of changes over time, whereby the observation of fluorescent lifetime distribution in a living body or the like is virtually impossible.

SUMMARY OF THE INVENTION

A scanning fluorescent microscope according to one aspect of the present invention includes a light source irradiating a sample with an exciting light pulse, and a splitter splitting fluorescent photons emitted from the sample excited by the exciting light pulse, in at least a first group and a second group. The scanning fluorescent microscope also includes a first detector detecting the fluorescent photons of the first group, a second detector detecting the fluorescent photons of the second group, a first counter counting a number of fluorescent photons detected by the first detector, a second counter counting a number of fluorescent photons detected by the second detector, a first correcting unit performing a predetermined correction to the number of fluorescent photons counted by the first counter, a second correcting unit performing a predetermined correction to the number of fluorescent photons counted by the second counter, an adder adding the numbers of fluorescent photons corrected by the first and second correcting units, and an operating unit calculating a florescent lifetime based on resulting numbers from the adder.

A scanning fluorescent microscope according to another aspect of the present invention includes a light source irradiating a sample with an exciting light pulse, a polarization splitter splitting fluorescent photons emitted from the sample excited by the exciting light pulse, in at least a first polarization component and a second polarization component. The scanning fluorescent microscope also includes a first detector detecting the fluorescent photons of the first polarization component, a second detector detecting the fluorescent photons of the second polarization component, a first counter counting a number of fluorescent photons detected by the first detector, a second counter counting a number of fluorescent photons detected by the second detector, a first correcting unit performing a predetermined correction to the number of fluorescent photons counted by the first counter, a second correcting unit performing a predetermined correction to the number of fluorescent photons counted by the second counter, and a polarization operating unit obtaining an orientation of the sample based on the numbers of fluorescent photons corrected by the first and second correcting units.

A scanning fluorescent microscope according to still another aspect of the present invention includes a light source irradiating a sample with an exciting light pulse, a splitter splitting fluorescent photons emitted from the sample excited by the exciting light pulse, in at least a first group and a second group, and a polarization splitter splitting the fluorescent photons of the first group in at least a first polarization component and a second polarization component. The scanning fluorescent microscope includes a first detector detecting the fluorescent photons of the first polarization component, a second detector detecting the fluorescent photons of the second polarization component, a first counter counting a number of fluorescent photons detected by the first detector, a second counter counting a number of fluorescent photons detected by the second detector, a first correcting unit performing a predetermined correction to the number of fluorescent photons counted by the first counter, a second correcting unit performing a predetermined correction to the number of fluorescent photons counted by the second counter, and a polarization operating unit obtaining an orientation of the sample based on the numbers of fluorescent photons corrected by the first and second correcting units.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a scanning fluorescent microscope according to the present invention will be explained in detail below with reference to the accompanying drawings.

Figure 1:
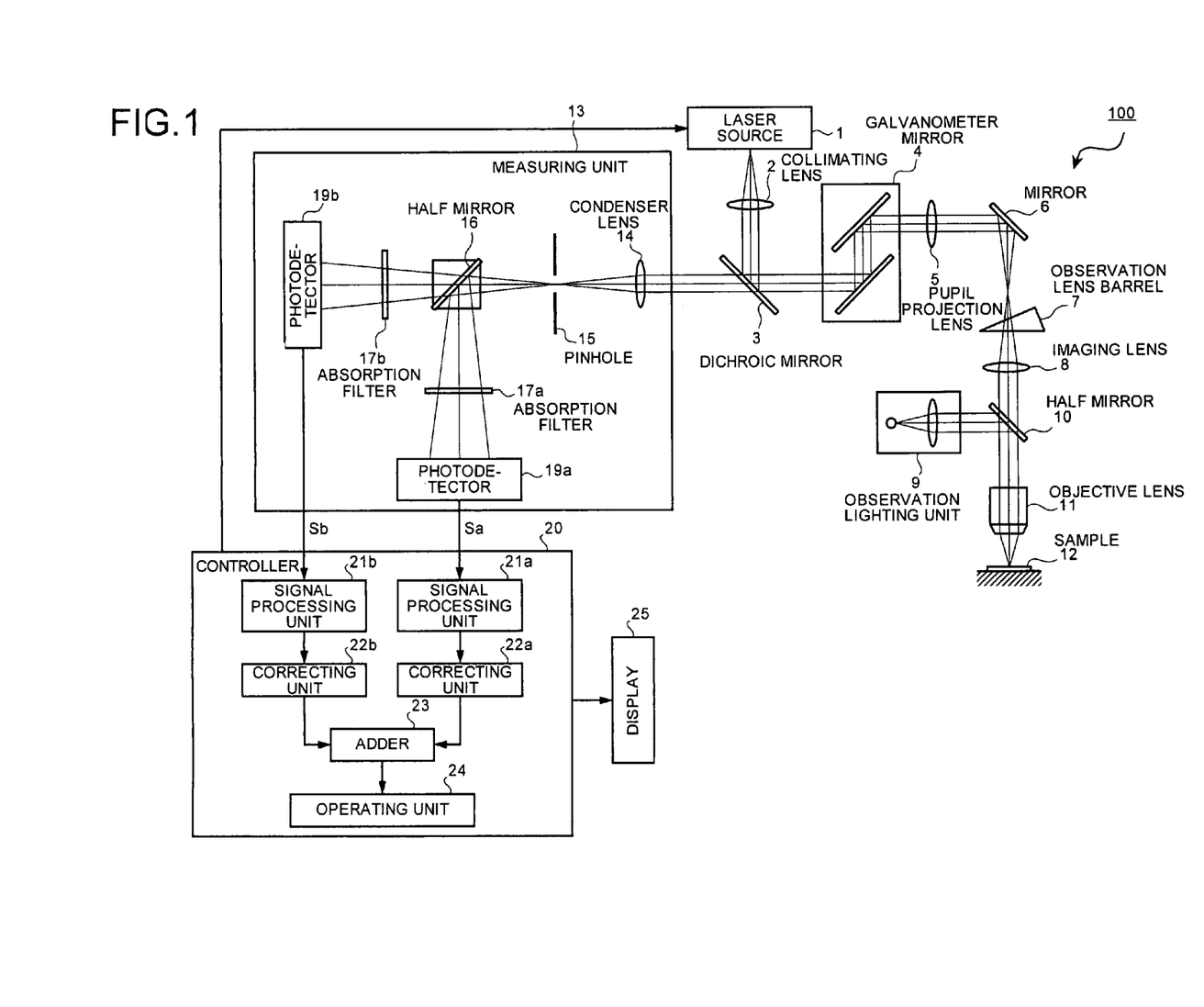
FIG. 1 is a schematic block diagram of a scanning fluorescent microscope according to a first embodiment of the present invention.

FIG. 1 is a block diagram of a schematic structure of a scanning fluorescent microscope 100 according to a first embodiment of the present invention. In FIG. 1, the scanning fluorescent microscope 100 includes a laser source 1, a collimating lens 2, a dichroic mirror 3, a galvanometer mirror 4, a pupil projection lens 5, a mirror 6, an observation lens barrel 7, an imaging lens 8, an observation lighting unit 9, a half mirror 10, an objective lens 11, a sample 12, a measuring unit 13, a controller 20, and a display 25.

The measuring unit 13 includes a condenser lens 14, a pinhole 15, a half mirror 16, absorption filters 17a and 17b, and photodetectors 19a and 19b. The controller 20 includes signal processing units 21a and 21b, correcting units 22a and 22b, an adder 23, and an operating unit 24.

Under the control by the controller 20, exciting light pulses are emitted from the laser source 1. The exciting light pulse is reflected by the dichroic mirror 3 via the collimating lens 2 to sequentially pass through the galvanometer mirror 4, the pupil projection lens 5, the mirror 6, the observation lens barrel 7, the imaging lens 8, the half mirror 10, and the objective lens 11, to be collected on the sample 12. The exciting light pulse thus focused on the sample excites the sample 12 to cause emission of fluorescent photons from the sample 12. The fluorescent photons emitted from the sample 12 move the optical path of the exciting light pulse backward from the objective lens 11 up to the dichroic mirror 3 and then pass through the dichroic mirror 3 to enter the measuring unit 13. After entering the measuring unit 13, the fluorescent photons sequentially pass through the condenser lens 14 and the pinhole 15 to enter the half mirror 16. The half mirror 16 reflects incoming fluorescent photons with the probability of 50% and transmits incoming fluorescent photons with the probability of 50%. For example, when one thousand fluorescent photons enter the half mirror 16, ideally five hundred fluorescent photons are reflected by the half mirror 16 to enter the photodetector 19a via the absorption filter 17a. The photodetector 19a outputs an electric signal Sa to the controller 20 for every incoming fluorescent photon. On the other hand, the remaining five hundred fluorescent photons not reflected by the half mirror 16 pass through the half mirror 16 to enter the photodetector 19b via the absorption filter 17b. The photodetector 19b outputs an electric signal Sb to the controller 20 for every incoming fluorescent photon.

The capacity of each of photodetectors 19a and 19b is restricted so that the emission rate of the fluorescent photons per irradiation would be equal to or less than 0.01 as described above, when a conventional Time-Correlated Single Photon Counting (TCSPC) is employed for the calculation of fluorescent lifetime without correction of the counted number of fluorescent photons. However, the detection of the fluorescent photons with the half mirror 16 and two photodetectors 19a and 19b allows the emission rate up to 0.02.

The signal processing units 21a and 21b in the controller 20 count the number of incoming electric signals Sa and Sb, respectively, at plural time gates which are set at various time period, to supply the counted numbers of fluorescent photons to the correcting units 22a and 22b, respectively. The correcting units 22a and 22b correct the received numbers of fluorescent photons in a predetermined manner to supply the resulting numbers to the adder 23. The adder 23 adds the corrected numbers of fluorescent photons and provides the resulting number of fluorescent photons to the operating unit 24. The operating unit 24 calculates the fluorescent lifetime based on the received sum of the numbers of fluorescent photons to supply the fluorescent lifetime to the display 25. The display 25 converts the received fluorescent lifetime into a display signal to output for display.

Figure 2:
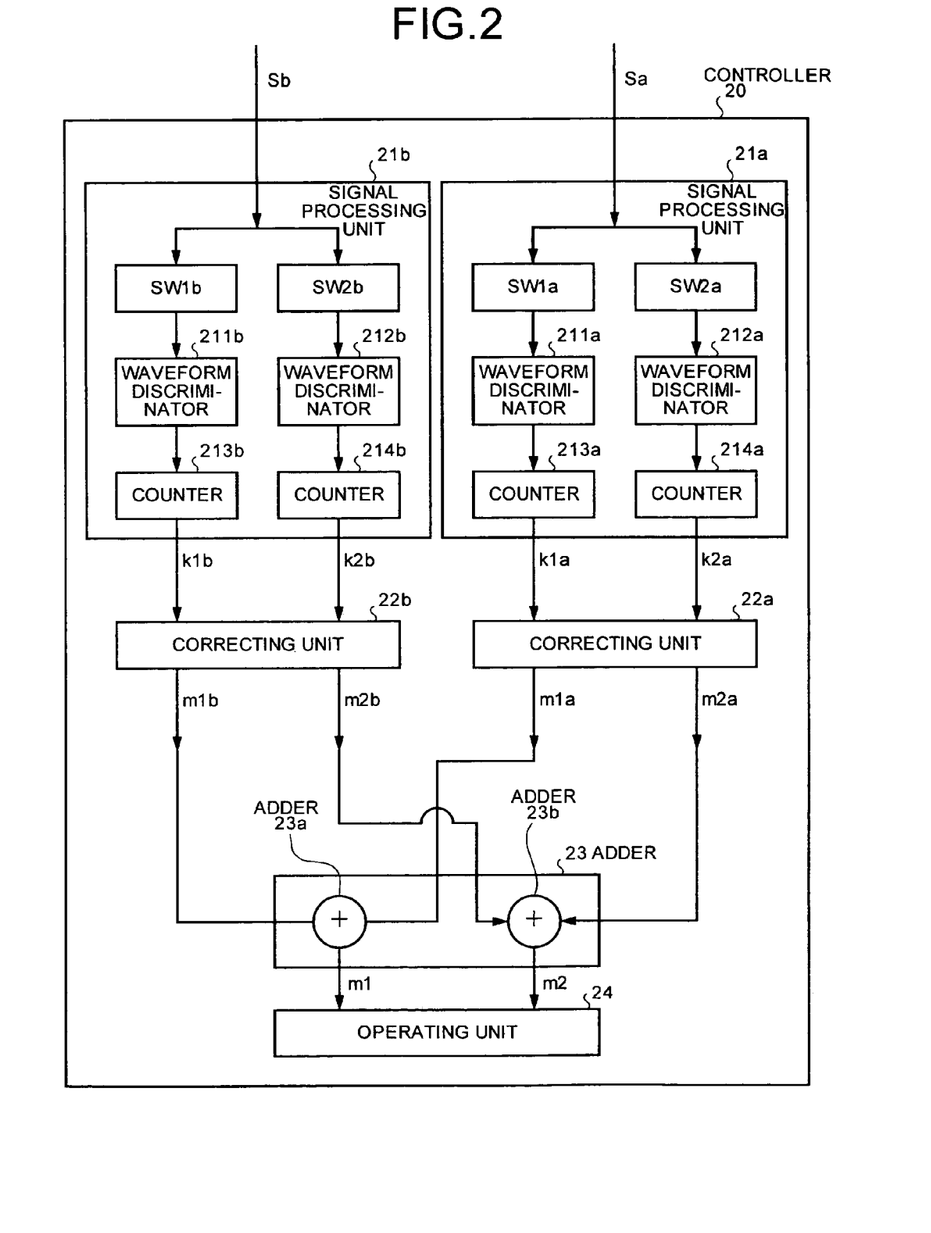
FIG. 2 is a detailed block diagram of a controller according to the first embodiment of the present invention.

Next, the correcting operation by the correcting units 22a and 22b will be described with reference to FIG. 2. FIG. 2 is a block diagram of a schematic structure of the controller 20. The controller 20 includes the signal processing units 21a and 21b, the correcting units 22a and 22b, the adder 23, and the operating unit 24. Further, the signal processing unit 21a includes switches SW1a and SW2a, waveform discriminators 211a and 212a, and counters 213a and 214a, whereas the signal processing unit 21b includes switches SW1b and SW2b, waveform discriminators 211b and 212b, and counters 213b and 214b.

While the photodetector 19a supplies the electric signal Sa to the signal processing unit 21a, the photodetector 19b supplies the electric signal Sb to the signal processing unit 21b. The timing of switching over between the "ON" state and the "OFF" state by the switches SW1a and SW1b is controlled in accordance with gate control signals from the controller 20. Only in the "ON" operation, the electric signals Sa and Sb are supplied to the counters 213a and 213b via the waveform discriminators 211a and 211b. The counters 213a and 213b count and output the numbers of fluorescent photons k1a and k1b to the correcting units 22a and 22b, respectively. The timing of switching over between the "ON" state and the "OFF" state by the switches SW2a and SW2b is controlled in accordance with gate control signals from the controller 20. Only in the "ON" operation, the electric signals Sa and Sb are supplied to the counters 214a and 214b via the waveform discriminators 212a and 212b, respectively. The counters 214a and 214b count and output the numbers of fluorescent photons k2a and k2b, to the correcting units 22a and 22b, respectively.

The correcting unit 22a corrects the received numbers of fluorescent photons k1a and k2a to numbers of fluorescent photons m1a and m2a to be supplied to the adder 23, whereas the correcting unit 22b corrects the received numbers of fluorescent photons k1b and k2b to numbers of fluorescent photons m1b and m2b to be supplied to the adder 23. The adder 23 includes adders 23a and 23b. The adder 23a adds the numbers of fluorescent photons m1a and m1b to output the resulting number of fluorescent photons m1 (=m1a+m1b) to the operating unit 24, whereas the adder 23b adds the numbers of fluorescent photons m2a and m2b to output the resulting number of fluorescent photons m2 (=m2a+m2b) to the operating unit 24. The operating unit 24 calculates the fluorescent lifetime based on the received numbers of fluorescent photons m1 and m2.

The correcting operation by the correcting units 22a and 22b will be described. In general, the emission rate of the fluorescent photons in the transition process of the sample 12 from the excited state to the ground state corresponds with the Poisson distribution. With an increase in the energy of exciting light, the emission rate of the fluorescent photons increases, and successive emission of fluorescent photons occurs, which tends to result in an increase in the measurement error of the number of fluorescent photons. However, if the measured number of fluorescent photons obtained in a state of high emission rate is corrected according to the Poisson distribution, the fluorescent lifetime can be calculated with little error. The correcting units 22a and 22b correct the measured numbers of fluorescent photons according to the Poisson distribution.

Assume that "$\mu$" represents the average number of incoming fluorescent photons among the fluorescent photons emitted from the sample 12 during a predetermined time gate $\Delta T$ per one irradiation of exciting light, and that "p (r, $\mu$)" represents the probability of the number of incoming fluorescent photons during the time gate $\Delta T$ being r. Then, the probability p(r, $\mu$) can be expressed by Equation (1):

$$p(r, \mu) = \frac{e^{-\mu} \cdot \mu^r}{r!} \quad (1)$$

Provided that r is equal to or larger than 1, Equation (1) leads to Equation (2).

$$p(r \geq 1, \mu) = 1 - p(0, \mu) = 1 - e^{-\mu} \quad (2)$$

Provided that "N" represents the number of irradiations of exciting light, and "k" represents the number of fluorescent photons measured at the time gate $\Delta T$, the average number "x" of fluorescent photons measured at the time gate $\Delta T$ (the number also referred to as 'count rate') can be expressed by "x=k/N". On the other hand, the probability p(0, $\mu$) that the fluorescent photons are not incident at the time gate $\Delta T$ can be expressed by Equation (3) where "x" represents the count rate:

$$p(0, \mu) = (N-k)/N = 1-x \quad (3)$$

Similarly, the probability p(0, $\mu$) that the fluorescent photons are not incident at time gate $\Delta T$ can be expressed by Equation (4) which is derived from Equation (1):

$$p(0, \mu) = e^{-\mu} \quad (4)$$

Hence, based on Equations (3) and (4), the average number $\mu$ of incoming fluorescent photons at the time gate $\Delta T$ can be expressed by Equation (5):

$$\mu = -\ln(1-x) \quad (5)$$

Here, provided that "m" represents the number of incoming fluorescent photons at the time gate $\Delta T$, "m" can be expressed as the multiplication of "N" and "$\mu$", where "N" is the number of irradiations of the exciting light and "$\mu$" is the average number of incoming fluorescent photons at the time gate $\Delta T$.

In other words, the correcting units 22a and 22b solve Equation (6) for "N" which is the number of irradiations by the laser source 1 and "k" which is the measured number of fluorescent photons input from the signal processing units 21a and 21b, and correct the measured number of fluorescent photons k to the number of actually incoming fluorescent photons m.

$$m = \sum_{r=1}^{\infty} r \cdot p(r, \mu) \cdot N = \mu \cdot N \quad (6)$$

The calculating operation by the operating unit 24 will be described. A first time gate $\Delta T1$ and a second time gate $\Delta T2$ are set as plural time gates. Provided that "k1" represents the measured number of fluorescent photons at the first time gate $\Delta T1$, "k2" represents the measured number of fluorescent photons at the second time gate $\Delta T2$, "t" represents the time difference between the start of the measurements for the first time gate $\Delta T1$ and the second time gate $\Delta T2$, and that the length of the first time gate $\Delta T1$ is equal to the length of the second time gate $\Delta T2$, the fluorescent lifetime $\tau$ can be expressed by Equation (7):

$$\tau = \frac{t}{\ln(k1/k2)} \quad (7)$$

Figure 3:
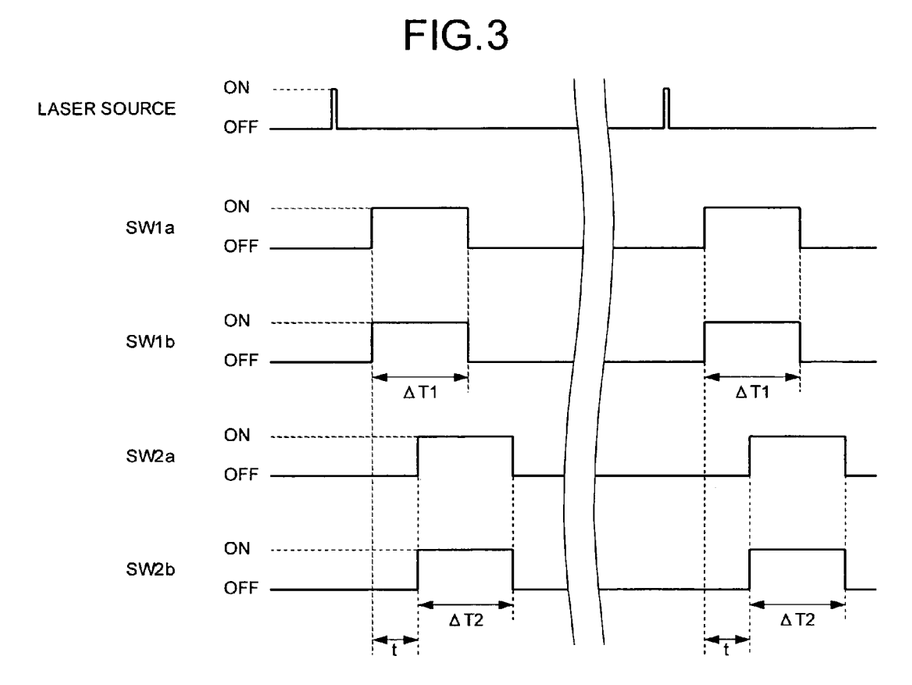
FIG. 3 is a timing chart of transition of a laser source and a switch between an "ON" state and an "OFF" state according to the first embodiment of the present invention.

FIG. 3 is a timing chart of the timing of transition between the "ON" operation and the "OFF" operation of the laser source 1 and of the switches SW1a, SW1b, SW2a, and SW2b. The controller 20 sets the time difference t of the first time gate $\Delta T1$ and the second time gate $\Delta T2$ through the control of the timing of incidence of the laser beam from the laser source 1 and the switches SW1a, SW1b, SW2a, and SW2b.

The correcting unit 22a corrects the measured numbers of fluorescent photons k1a and k2a to the numbers m1a and m2a through the calculation of Equation (6) to output to the adder 23, whereas the correcting unit 22b corrects the measured numbers of fluorescent photons k1b and k2b to the numbers m1b and m2b through the calculation of Equation (6) to output to the adder 23. The adder 23a in the adder 23 adds the numbers of fluorescent photons m1a and m1b to output the number of incoming fluorescent photons m1 (=m1a+m1b) at the first time gate $\Delta T1$ to the operating unit 24, whereas the adder 23b in the adder 23 adds the numbers of fluorescent photons m2a and m2b to output the number of incoming fluorescent photons m2 (=m2a+m2b) at the second time gate $\Delta T2$ to the operating unit 24.

The operating unit 24 solves Equation (8) for the received values of m1 and m2 to calculate the fluorescent lifetime $\tau$:

$$\tau = \frac{t}{\ln(m1/m2)} \quad (8)$$

In the first embodiment, the half mirror 16 serves to separate the fluorescent photons to allow the accurate and sequential measurement of the fluorescent photons. With the correction of the numbers of photons measured by respective photodetectors 19a and 19b according to the Poisson distribution, which is the emission rate of the fluorescent photons, even when the count rate is increased from 0.01 as in the conventional technique to approximately 1, the calculation of the fluorescent lifetime is possible without the increase in errors. Then, the enhancement of the intensity of the exciting light pulse is allowed. Thus, with the half mirror 16 and the correction of the number of fluorescent photons, the count rate can be further increased to approximately as high as 2. In other words, the calculation of the fluorescent lifetime can be performed at nearly 200 times faster than the conventional technique.

In addition, though in the first embodiment the length of the first time gate ΔT1 is set to be equal to the length of the second time gate ΔT2, they may not be equal. Still in addition, though in the first embodiment the time difference t of the start of the measurement is set to be smaller than the first time gate ΔT1, the time difference t may not be smaller as far as the time difference t is constant.

Figure 4:
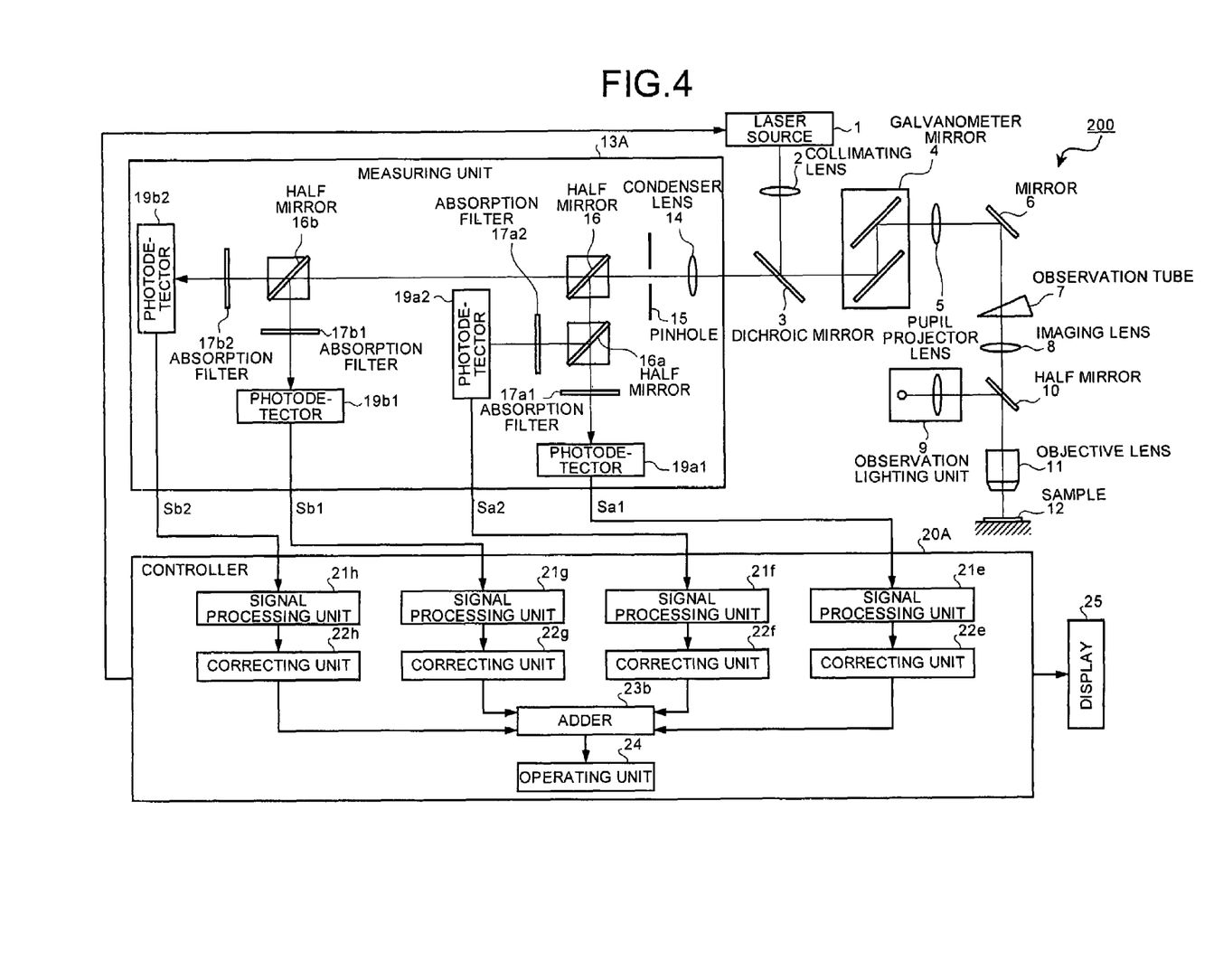
FIG. 4 is a schematic block diagram of a scanning fluorescent microscope according to a modification of the first embodiment of the present invention.

Next, a modification of the first embodiment will be described. In the first embodiment, one half mirror is arranged to separate the fluorescent photons to shorten the time for measuring the number of fluorescent photons to ½. In the modification, three half mirrors are arranged to further shorten the time for measuring the number of fluorescent photons to ¼.

FIG. 4 is a block diagram of a schematic structure of a scanning fluorescent microscope 200 as a modification of the first embodiment of the present invention. In FIG. 4, a measuring unit 13A includes half mirrors 16a and 16b arranged at a subsequent stage of the half mirror 16, and absorption filters 17a1, 17a2, 17b1, and 17b2, and photodetectors 19a1, 19a2, 19b1, and 19b2, arranged at a subsequent stage of the half mirrors 16a and 16b. A controller 20A includes signal processing units 21e, 21f, 21g, and 21h, correcting units 22e, 22f, 22g, and 22h, the adder 23b and the operating unit 24. The same components with FIG. 1 are denoted with the same reference characters.

The fluorescent photons coming into the half mirror 16 is split by the half mirror 16 and then by the half mirrors 16a and 16b. Hence, the photodetectors 19a1, 19a2, 19b1, and 19b2 output the electric signals Sa1, Sa2, Sb1, and Sb2, respectively, representing the four divided fluorescent photons. Signal processing units 21e, 21f, 21g, and 21h receive the electric signals Sa1, Sa2, Sb1, and Sb2, respectively, to measure the number of fluorescent photons and output the measured number of fluorescent photons to the correcting units 22e, 22f, 22g, and 22h, respectively. The correcting units 22e, 22f, 22g, and 22h correct the received numbers of fluorescent photons according to the Poisson distribution and supply the corrected numbers of fluorescent photons to the adder 23b. The adder 23b adds the received numbers of fluorescent photons to output the result to the operating unit 24. The operating unit 24 calculates the fluorescent lifetime based on the received numbers of fluorescent photons.

In the modification of the first embodiment, three half mirrors 16, 16a, and 16b are arranged to split the fluorescent photons into four parts. Thus, the time required for the measurement of fluorescent photons can be made quarter the time required in the conventional technique.

In the modification of the first embodiment, the half mirrors 16, 16a, and 16b are arranged to split the fluorescent photons into four parts, thereby shortening the measurement time of the number of fluorescent photons to quarter the conventional technique. However, more than three half mirrors may be arranged to further shorten the time required for measurement of the number of fluorescent photons.

Figure 5:
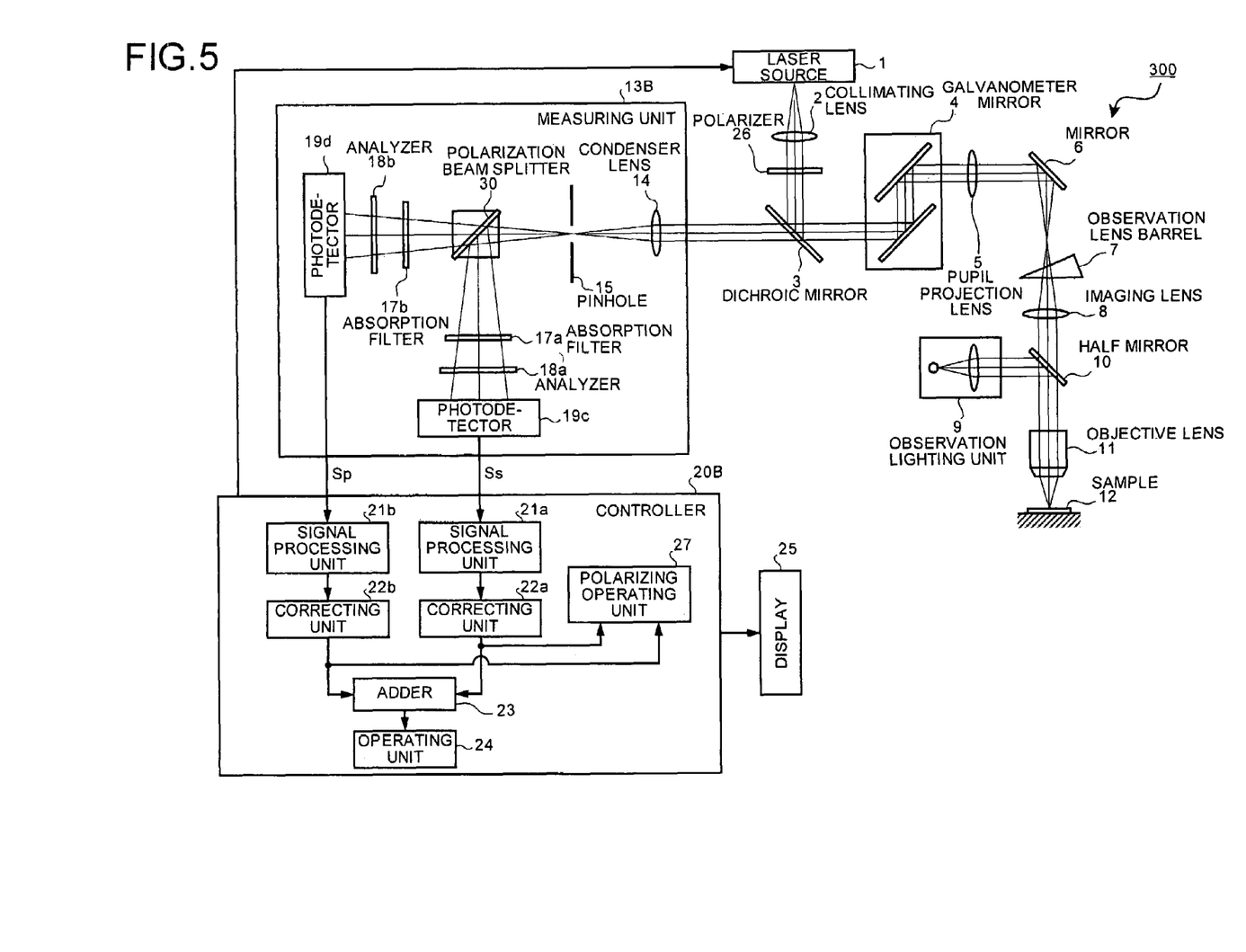
FIG. 5 is a schematic block diagram of a scanning fluorescent microscope according to a second embodiment of the present invention.

Next, a second embodiment will be described. In the first embodiment, the half mirror 16 is arranged to shorten the time of measurement of the number of fluorescent photons. In the second embodiment, a polarization beam splitter is arranged to shorten the time for measurement of the number of fluorescent photons as well as to allow the measurement of the orientation of a fluorescent molecule in the sample.

FIG. 5 is a block diagram of a schematic structure of a scanning fluorescent microscope 300 according to the second embodiment. In FIG. 5, the scanning fluorescent microscope 300 includes a polarizer 26 arranged between the collimating lens 2 and the dichroic mirror 3 to enhance the linearity of the exciting light, and a polarization beam splitter 30 instead of the half mirror 16. Further, analyzers 18a and 18b are arranged to supplant the limitation of polarizing characteristics of the polarization beam splitter 30. Further, a controller 20B includes a polarizing operating unit 27. The same components with FIG. 1 are denoted with the same reference characters.

As shown in FIG. 5, the exciting light pulse emitted from the laser source 1 is polarized by the polarizer 26 to a predetermined angle of polarization and directed to the sample 12. When the fluorescent photon in the sample 12 has a transition moment, the sample would be excited only with the polarized light parallel to the transition moment and the fluorescence which is emitted during the transition from the excited state to the ground state is also parallel to the transition moment. Hence, when the polarization angle of the light polarized by the polarizer 26 is parallel with the transition moment of the fluorescent photon in the sample 12, the polarized fluorescence is emitted from the sample 12.

The polarized fluorescence emitted from the sample 12 moves the optical path of the exciting light pulse backwards from the objective lens 11 to the dichroic mirror 3 to enter a measuring unit 13B. The fluorescence entering the measuring unit 13B passes sequentially through the condenser lens 14 and the pinhole 15 to enter the polarization beam splitter 30. The polarization beam splitter 30 polarizes the incident light by 90° (P-polarization) to generate transmissive light and polarizes the incident light by 0° (S-polarization) to generate reflective light. Hence, when the polarization angle of the incoming fluorescence into the polarization beam splitter 30 is 45°, the light is P-polarized with the probability of 50% and S-polarized with the probability of 50%. In other words, N fluorescent photons with 45° polarization angle are split in P-polarized portion and S-polarized portion each consisting of N/2 photons.

The S-polarized fluorescent photons enter a photodetector 19c via the absorption filter 17a and the analyzer 18a, whereas the P-polarized fluorescent photons enter a photodetector 19d via the absorption filter 17b and the analyzer 18b. The photodetector 19c outputs an electric signal Ss to the signal processing unit 21a for every incoming fluorescent photon, whereas the photodetector 19d outputs an electric signal Sp to the signal processing unit 21b for every incoming fluorescent photon.

This embodiment as shown in FIG. 5 has the following advantageous functions. After the input of the electric signals Ss and Sp to the signal processing units 21a and 21b, the correcting units 22a and 22b correct the counted number of fluorescent photons. To complete one function, for example, these corrected numbers of fluorescent photons are supplied sequentially to the adder 23 and the operating unit 24 and used to calculate the conventional fluorescent lifetime in a manner as mentioned above. And to complete another function, each polarized corrected numbers of fluorescent photons are supplied to the polarizing operating unit 27 for the calculation of the numbers of fluorescent photons and/or lifetimes respectively. A lot of information such as the dynamics of a molecular movement, transition moment and a molecular orientation of a fluorescent molecule are obtained from these data sets. A display 25 selects and displays an image relating to the fluorescent lifetime and an image relating to the S-polarization and the P-polarization under the control of the controller 20B.

In the second embodiment, with the arrangement of the polarizer 26 and the polarization beam splitter 30, the fluorescent photons are split in two parts to shorten the time of measurement of the number of fluorescent photons to half. Further, with the display of the polarized fluorescent photons, the orientation of the fluorescent molecule in the sample 12 can be observed.

In the second embodiment, only one display 25 is provided to select and output the image of fluorescent lifetime distribution and the image relating to the polarization. However, two displays may be provided to constantly output and display two types of images.

Figure 6:
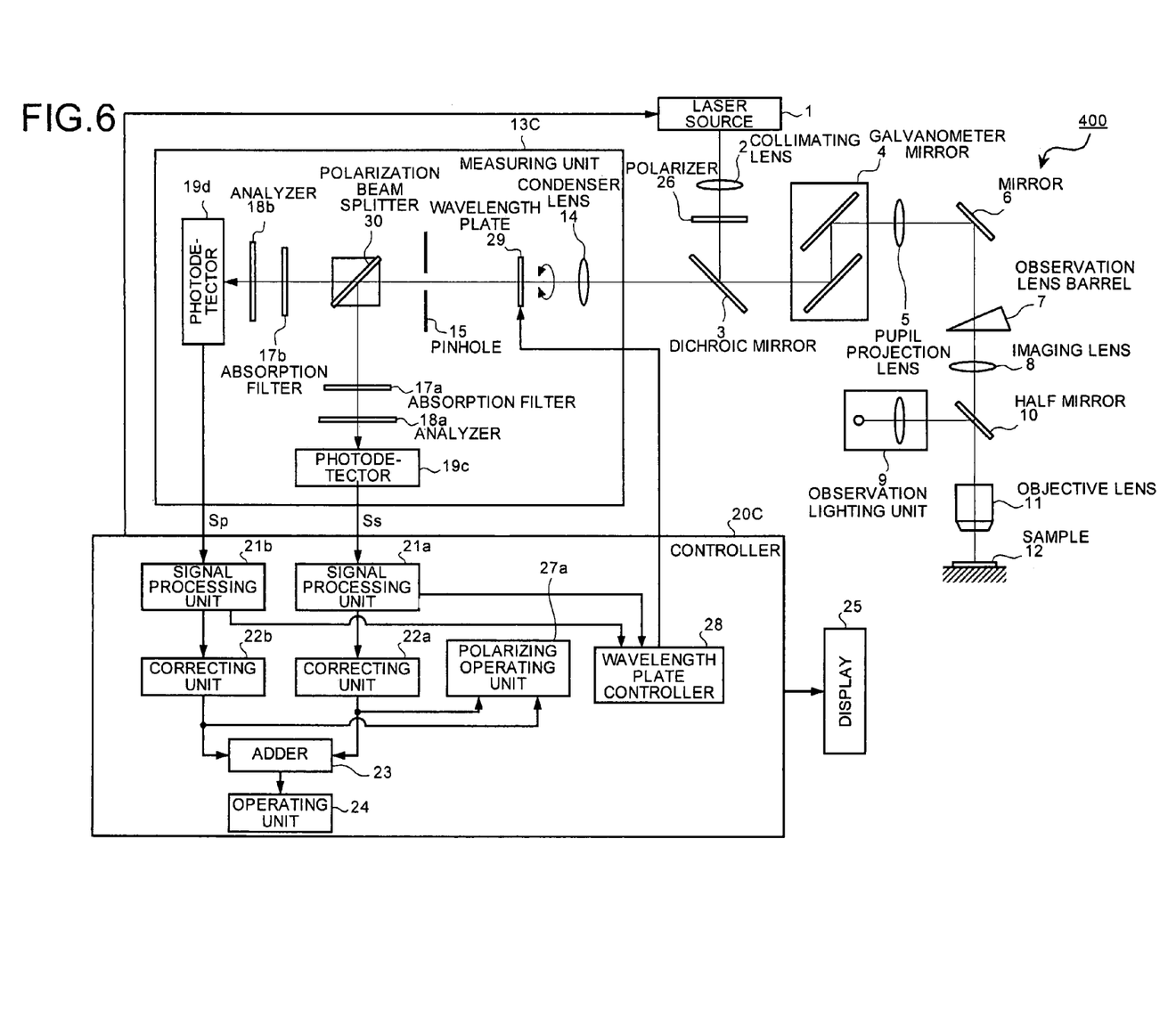
FIG. 6 is a schematic block diagram of a scanning fluorescent microscope according to a modification of the second embodiment of the present invention.

Next, a modification of the second embodiment will be described. In the second embodiment, the polarization beam splitter 30 is arranged to shorten the time for measuring the number of fluorescent photons to half and to allow the observation of orientation of the fluorescent molecules. In the modification, however, a wavelength plate is arranged between the condenser lens 14 and the pinhole 15 to accommodate the change in the polarization angle of the fluorescence, so that the polarization angle of the fluorescence incident on the polarization beam splitter 30 can be adjusted.

FIG. 6 is a block diagram of a schematic structure of a scanning fluorescent microscope 400 according to the modification of the second embodiment. In FIG. 6, a measuring unit 13C includes a ½ wavelength plate 29 as a polarization direction rotating unit between the condenser lens 14 and the pinhole 15, and a controller 20C includes a wavelength plate controller 28. The wavelength plate controller 28 controls the rotation of the ½ wavelength plate 29. The same components as in FIG. 5 are denoted by the same reference characters.

The ½ wavelength plate 29 shifts the phase of the vertical polarization axis based on the difference in refractive indices of the horizontal polarization and the vertical polarization to change the angle of polarization of the incoming light. Though the polarization angle of the fluorescence emitted from the sample 12 is determined by the polarizer 26, when the sample 12 is a living body, the polarization angle of the fluorescence might change. When the polarization angle of the fluorescence shifts from 45°, the probability of S-polarization and the probability of P-polarization at the polarization beam splitter 30 would not be the same, in other words, the fluorescent photons would not be equally split. To prevent such inconvenience, the polarization angle of the fluorescence is rotated by the wavelength plate 29 for adjustment so that the polarization angle of the incoming fluorescence to polarization beam splitter 30 is always maintained at 45°. The wavelength plate controller 28 receives the signals from the signal processing units 21a and 21b and controls the rotation angle of the ½ wavelength plate 29 so that the outputs from the photodetectors 19c and 19d are equal to each other.

In the modification, the ½ wavelength plate 29 serves to adjust the polarization angle of the incoming fluorescence into the polarization beam splitter 30 so that the change in the transition moment of the fluorescent molecule in the sample 12 can be accommodated. Thus, the fluorescent photons entering the polarization beam splitter 30 can be equally split and the accurate and high-speed measurement of the fluorescent lifetime is allowed.

Figure 7:
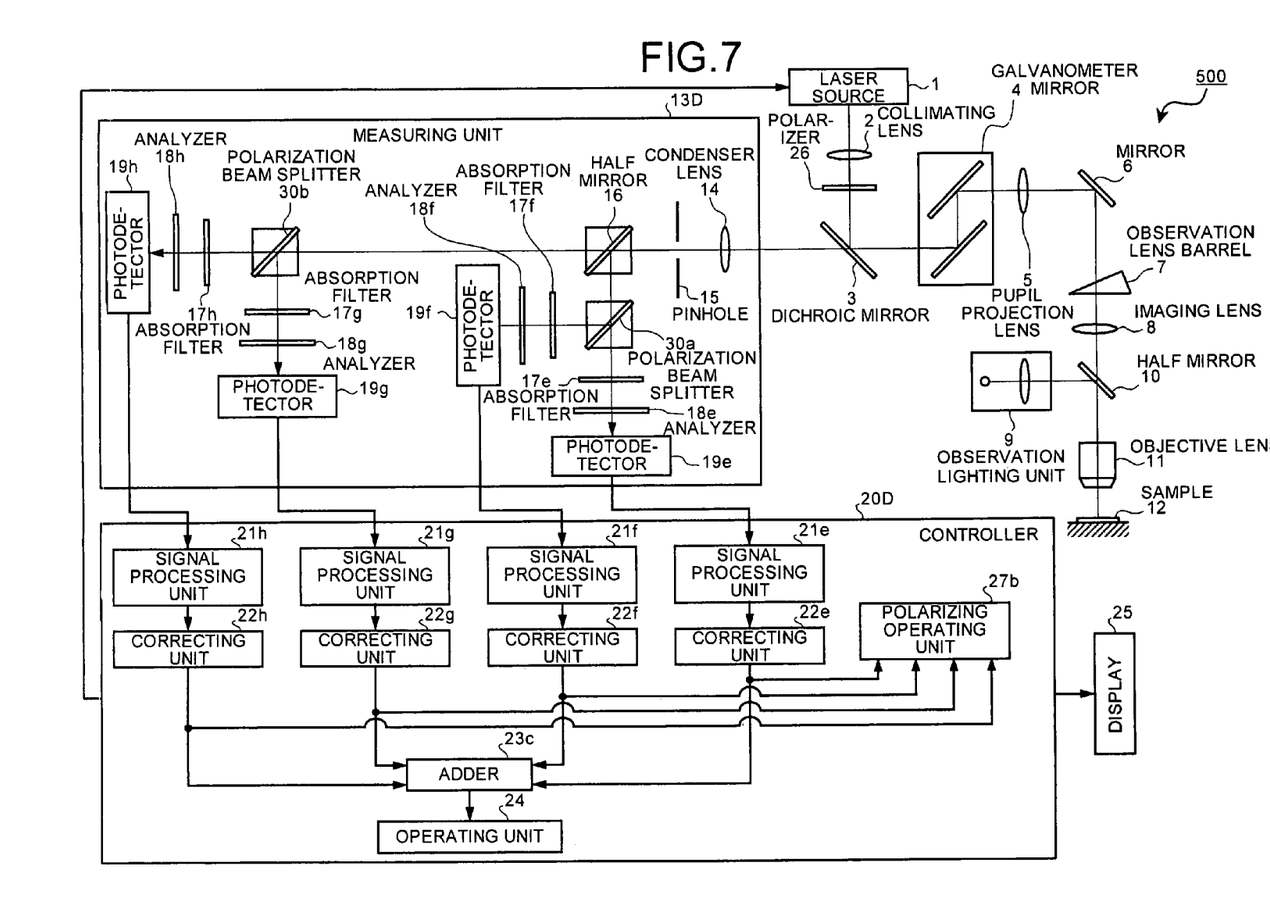
FIG. 7 is a schematic block diagram of a scanning fluorescent microscope according to a third embodiment of the present invention.

Next, a third embodiment will be described. In the first embodiment, the half mirror 16 is arranged, and in the second embodiment the polarization beam splitter 30 is arranged to split the fluorescent photons to shorten the time of measurement of the number of fluorescent photons. In the third embodiment, however, a combination of the half mirror and the polarization beam splitter is arranged to shorten the time of measurement of the number of fluorescent photons as well as to allow the observation of the orientation of fluorescent molecule.

FIG. 7 is a block diagram of a schematic structure of a scanning fluorescent microscope 500 according to the third embodiment. In FIG. 7, the scanning fluorescent microscope 500 includes the polarizer 26 arranged between the collimating lens 2 and the dichroic mirror 3, and polarization beam splitters 30a and 30b arranged at a subsequent stage of the half mirror 16. Further, a controller 20D includes a polarizing operating unit 27b. The same components with FIG. 4 are denoted with the same reference characters.

As shown in FIG. 7, the exciting light pulse emitted from the laser source 1 is polarized to a predetermined polarization angle by the polarizer 26 to be directed to the sample 12. The sample 12 emits the polarized fluorescence which enters a measuring unit 13D, sequentially passes through the condenser lens 14 and the pinhole 15, and then enters the half mirror 16. The half mirror 16 splits the incoming fluorescent photons regardless of the polarization angle leaving the polarization angles as they are. The split polarized fluorescent photons enter the polarization beam splitters 30a and 30b in a subsequent stage, respectively. The polarization beam splitters 30a and 30b split the incoming fluorescent photons in two parts depending on the polarization angle. Thus, the fluorescent photons entering the measuring unit 13D are split eventually in four parts.

Four groups of fluorescent photons after splitting pass through absorption filters 17e, 17f, 17g, and 17h, analyzers 18e, 18f, 18g, and 18h, and photodetectors 19e, 19f, 19g, and 19h, respectively to be converted into electric signals. The electric signals are received and processed by the signal processing units 21e, 21f, 21g, and 21h, the correcting units 22e, 22f, 22g, and 22h, the adder 23c, and the operating unit 24 for the calculation of the fluorescent lifetime. On the other hand, the corrected numbers of fluorescent photons output from the correcting units 22e, 22f, 22g, and 22h are supplied into the polarizing operating unit 27b for the calculation of the numbers of fluorescent photons which are S-polarized and P-polarized.

In the third embodiment, with the arrangement of the half mirror 16 and the polarization beam splitters 30a and 30b in a subsequent stage of the half mirror 16, the time for measuring the number of fluorescent photons is shortened to ¼. At the same time, the measurement of the orientation of fluorescent molecule in the sample 12 is allowed.

In the third embodiment, one half mirror 16 is arranged and two polarization beam splitters 30a and 30b are arranged in a subsequent stage of the half mirror 16. However, more than one half mirrors may be arranged and the polarization beam splitter may be arranged at the last stage.

Further, a wavelength plate may be arranged between the condenser lens 14 and the pinhole 15 to accommodate the change in the polarization angle of fluorescence so that the polarization angle of the incoming fluorescence to the polarization beam splitters 30a and 30b is constant.

Still further, though in the second and the third embodiments, the polarizer 26 is employed to enhance the linearity of polarization of the exciting light pulse, the use of polarizer 26 may not be necessary when the exciting light source provides highly linearly polarized laser beam.

As described above, the scanning fluorescent microscope according to any one of the embodiments has advantages of calculating the fluorescent lifetime with little error in a short time by using a splitter guiding the fluorescent photons to several optical paths.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A scanning fluorescent microscope, comprising:
   a light source which irradiates a sample with an exciting light pulse;
   a splitter which splits fluorescent photons emitted from the sample excited by the exciting light pulse into at least a first group and a second group;
   a first detector which detects the fluorescent photons of the first group;
   a second detector which detects the fluorescent photons of the second group;
   a first counter which counts a number of fluorescent photons detected by the first detector;
   a second counter which counts a number of fluorescent photons detected by the second detector;
   a first correcting unit which performs a predetermined correction to the number of fluorescent photons counted by the first counter;
   a second correcting unit which performs the predetermined correction to the number of fluorescent photons counted by the second counter;
   an adder which adds the numbers of fluorescent photons corrected by the first and second correcting units; and
   an operating unit which calculates a fluorescent lifetime based on data output from the adder.

2. The scanning fluorescent microscope according to claim 1, wherein the first and second correcting units perform the predetermined correction according to a Poisson distribution.

3. The scanning fluorescent microscope according to claim 1, wherein the splitter includes a half mirror.

4. The scanning fluorescent microscope according to claim 1, wherein the splitter includes a plurality of half mirrors that split the fluorescent photons into at least three approximately equal groups.

5. A scanning fluorescent microscope, comprising:
   a light source which irradiates a sample with an exciting light pulse;
   a polarization splitter which splits fluorescent photons emitted from the sample excited by the exciting light pulse into at least a first polarization component and a second polarization component;
   a first detector which detects the fluorescent photons of the first polarization component;
   a second detector which detects the fluorescent photons of the second polarization component;
   a first counter which counts a number of fluorescent photons detected by the first detector;
   a second counter which counts a number of fluorescent photons detected by the second detector;
   a first correcting unit which performs a predetermined correction to the number of fluorescent photons counted by the first counter;
   a second correcting unit which performs the predetermined correction to the number of fluorescent photons counted by the second counter;
   a polarization operating unit which obtains an orientation of the sample based on the numbers of fluorescent photons corrected by the first and second correcting units;
   an adder which adds the numbers of fluorescent photons corrected by the first and second correcting units; and
   an operating unit which calculates a fluorescent lifetime based on data output from the adder.

6. The scanning fluorescent microscope according to claim 5, wherein the first and second correcting units perform the predetermined correction according to a Poisson distribution.

7. The scanning fluorescent microscope according to claim 5, wherein the polarization splitter includes a polarization beam splitter that reflects an S-polarization component of the fluorescent photons and transmits a P-polarization component of the fluorescent photons.

8. The scanning fluorescent microscope according to claim 5, further comprising a polarizer which linearly polarizes the exciting light pulse.

9. The scanning fluorescent microscope according to claim 5, further comprising a polarization direction rotating unit which rotates a polarization angle of the fluorescence emitted from the sample such that the polarization splitter splits the fluorescent photons approximately equally.

10. The scanning fluorescent microscope according to claim 9, wherein the polarization direction rotating unit includes a ½ wavelength plate.

11. A scanning fluorescent microscope, comprising:
    a light source which irradiates a sample with an exciting light pulse;
    a splitter which splits fluorescent photons emitted from the sample excited by the exciting light pulse into at least a first group and a second group;
    a polarization splitter which splits the fluorescent photons of the first group into at least a first polarization component and a second polarization component;
    a first detector which detects the fluorescent photons of the first polarization component;
    a second detector which detects the fluorescent photons of the second polarization component;
    a first counter which counts a number of fluorescent photons detected by the first detector;
    a second counter which counts a number of fluorescent photons detected by the second detector;
    a first correcting unit which performs a predetermined correction to the number of fluorescent photons counted by the first counter;
    a second correcting unit which performs the predetermined correction to the number of fluorescent photons counted by the second counter;
    a polarization operating unit which obtains an orientation of the sample based on the numbers of fluorescent photons corrected by the first and second correcting units;
    an adder which adds the numbers of fluorescent photons corrected by the first and second correcting units; and
    an operating unit which calculates a fluorescent lifetime based on data output from the adder.

12. The scanning fluorescent microscope according to claim 11, wherein the first and second correcting units perform the predetermined correction according to a Poisson distribution.

13. The scanning fluorescent microscope according to claim 11, wherein the splitter includes a half mirror.

14. The scanning fluorescent microscope according to claim 11, wherein the splitter includes a plurality of half mirrors that split the fluorescent photons into at least three approximately equal groups.

15. The scanning fluorescent microscope according to claim 11, wherein the polarization splitter includes a polarization beam splitter that reflects an S-polarization component of the fluorescent photons and transmits a P-polarization component of the fluorescent photons.

16. The scanning fluorescent microscope according to claim 11, further comprising a polarizer which linearly polarizes the exciting light pulse.

17. The scanning fluorescent microscope according to claim 11, further comprising a polarization direction rotating unit which rotates a polarization angle of the fluorescence emitted from the sample such that the polarization splitter splits the fluorescent photons of the first group approximately equally.

18. The scanning fluorescent microscope according to claim 17, wherein the polarization direction rotating unit includes a ½ wavelength plate.

* * * * *